United States Patent [19]

Thoma

[11] 4,235,865
[45] Nov. 25, 1980

[54] METHOD FOR THE DETERMINATION OF UNBOUND HORMONES AND PHARMACEUTICALS

[75] Inventor: Hans A. Thoma, Munich, Fed. Rep. of Germany

[73] Assignee: Chandon Investment Planning Ltd., Grand Cayman, Cayman Islands

[21] Appl. No.: 899,706

[22] Filed: Apr. 24, 1978

[30] Foreign Application Priority Data

Jul. 8, 1977 [DE] Fed. Rep. of Germany ....... 2731028

[51] Int. Cl.$^2$ ......................... B01N 33/16; G21H 5/02
[52] U.S. Cl. ...................................... 424/1; 23/230 B; 424/12
[58] Field of Search ..................... 424/1, 12; 73/230 B

[56] References Cited

U.S. PATENT DOCUMENTS

| | | | |
|---|---|---|---|
| 3,966,897 | 6/1976 | Renn et al. ................................ | 424/1 |
| 4,039,652 | 8/1977 | Adams et al. ............................ | 424/1 |
| 4,061,466 | 12/1977 | Sjöholm et al. .......................... | 424/1 |

OTHER PUBLICATIONS

Goodfriend et al., Immunochemistry, vol. 6, May, 1969, pp. 481-484.

Primary Examiner—Benjamin R. Padgett
Assistant Examiner—Christine M. Nucker
Attorney, Agent, or Firm—Schwartz, Jeffery, Schwaab, Mack, Blumenthal & Koch

[57] ABSTRACT

Disclosed is a method for the determination of unbound hormones and pharmaceuticals comprising placing a solution containing unbound hormones, hormones bound to bonding proteins and bonding proteins into contact with an immobilized antibody; reacting the unbound hormone with the antibody; eluting the hormones bound to bonding proteins and the bonding hormones with a solution containing a marked hormone; reacting the marked hormone with the antibody; eluting the marked hormone not reacted with the antibody, and determining the marked hormone by radioimmunological evaluation.

12 Claims, 1 Drawing Figure

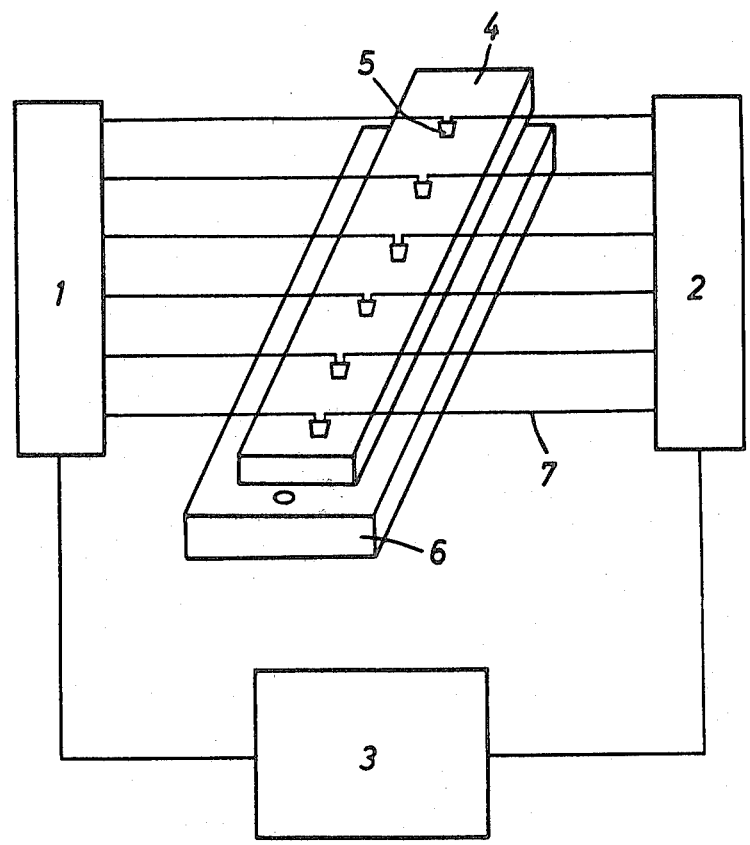

METHOD FOR THE DETERMINATION OF UNBOUND HORMONES AND PHARMACEUTICALS

TECHNICAL FIELD OF THE INVENTION

This invention relates to a method for the determination of unbound hormones or pharmaceuticals. More specifically, the invention relates to the reaction of unbound hormones or pharmaceuticals with an antibody followed by determination by means of radioimmunological evaluations.

BACKGROUND OF THE PRIOR ART

Steroids in human serum are bound to proteins. In clinical chemical hormone analysis, hormone determinations are based almost entirely on the principle of dissolving the bond between the transport hormones and the hormones and to measure the total concentration of the hormone. The techniques used to dissolve the bonds may be of the most varied types, such as, solvent extraction, heat denaturization, enzymatic hydrolysis and the treatment with acids or alkalis.

However, the content of bonding proteins in the human serum is not always of the same magnitude. It is known, for example, that female patients under antiovulation therapy or during late pregnancy exhibit clearly higher values of cortisol-binding globulin or thyroxine-binding globulin. Other examples include the isolated controversial increases or decreases in bonding protein contents found in different individuals of related familial background and heredity.

Bonding protein levels varying in this manner often result in the determination of total hormones to values which indicate a certain syndrome, while the patients do not show the clinical image of the corresponding syndrome. Apparently, this is due to the fact that the results reflect only the portion not bound to proteins, while the portion bound to the protein is biologically inactive.

The known techniques of the determination of protein-bound or free hormones are either those in which the equilibrium between the bound and free hormones is maintained during the separation, such as, for example, in classical equilibrium dialysis or ultrafiltration, or those in which the equilibrium is not maintained during the separation, such as, for example, column chromatography or adsorption methods. These techniques, nevertheless, yield a measure of the portion of the hormones that is actually free. In these techniques, the reaction time is a critical factor because the bond between the adsorbing agent and the steroid is irreversible.

Among the disadvantages of the known separation methods is that they are very expensive and yield only the percentual proportion of the free hormone. The absolute value must be calculated through the additional determination of total hormone concentration. Because of this indirect determination, measurements become correspondingly inaccurate, aside from the highly expensive techniques required to determine the percentual proportion.

SUMMARY OF THE INVENTION

Among the objects of the invention is to provide a method for the determination of unbound hormones or pharmaceuticals suitable for the determination of the absolute concentration of free hormones and not merely of their percentual proportion. Further, the method should be simple and lend itself to automation.

These objects are accomplished through the present invention by presenting a method for the determination of unbound hormones or pharmaceuticals by the reaction of the hormones or pharmaceuticals with an antibody followed by radioimmunological evaluation, wherein a solution containing unbound hormones, hormones bound to bonding proteins and bonding hormones is added to an immobilized antibody. The unbound hormone is allowed to react with the antibody, while the hormone bound to proteins and the bonding proteins are eluted with a solution containing a marked hormone, with the marked hormone being allowed to react with the antibody, and any of the marked hormone not reacting with the antibody being eluted, followed by the determination of the marked hormone.

DETAILED DESCRIPTION OF THE INVENTION

The method of the invention renders possible the determination of the absolute concentration of unbound hormones or pharmaceuticals in a single process. The method of determination is extremely simple, rapid and capable of automation.

The method of the invention is based on the following principle. In sera and plasma, the hormone or pharmaceutical (H) is in thermodynamic equilibrium, following the mass action law with the transporting protein (B):

$$H + B \rightleftharpoons HB$$

If the serum is placed upon the dried antibody gel powder, the matrix begins to swell strongly. This swelling process, which proceeds very rapidly, results in the separation of the diffusible free hormone and of the hormone/bonding protein complex. During the swelling process, due to the small pore size of the matrix, only relatively small molecules are able to penetrate the matrix. The small free hormone is taken up by the liquid inside the gel $V_i$, while the proteins and the protein-bound hormones, because of the small pore size of the gel, are able to utilize only the outer volume $V_a$ surrounding the gel particles. Accordingly, the swelling process results in practice in an extremely rapid, complete separation of free and bound hormones.

Because volume $V_i$ comprising approximately 80 to 90% of the total gel volume contains the antibody, the reaction of the antibody with the inflowing hormone takes place in volume $V_i$ as follows:

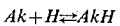

$$Ak + H \rightleftharpoons AkH$$

In a second step, elution continues only until the external particle volume $V_a$ is eluted. Among others, $V_a$ also contains the bonding protein and the hormone/bonding protein complex.

Following the swelling process, the diffusable hormone is found mainly in the internal gel particle volume $V_i$. During the swelling process, the antibody has already reacted with the hormone. Further, the volume $V_i$ is substantially greater than $V_a$. For these reasons, the elution which involves only the outer volume of gel particle $V_a$ will wash away only a slight amount of the diffusable hormone from the gel.

If the elution of the hormone/binding protein complex is effected with a solution containing a marked hormone, then in a second reaction the antibody not yet complexed with the unmarked hormone, can be determined with the marked hormone.

Because the reactions of the unmarked hormone and the marked hormone are subsequent to each other, it is not necessary during the incubation with the marked hormone to await the establishment of the equilibrium. After a certain period of time, the hormone bound to the antibody and the unbound hormone can be separated by elution with a buffer solution.

The concentration of the marked hormone can be measured in the elute or in the gel in a known manner such as by the radioimmunoassay technique. The radioimmunological determination of unmarked hormones is also known. A detailed description of radioimmune assay is found, for example, in *Clinical Chemistry*, Vol. 19, No. 2, 1973, p. 145. Alternatively, other methods of determination, such as fluoroimmunological determination or determination by means of enzymatic marking, may also be considered.

The method of the invention is suitable for the determination of different hormones and pharmaceuticals present in sera or plasma bound in part to specific or nonspecific bonding proteins. These may consist of thyroid hormones, particularly, thyroxine and tri-iodothyroxine, the steroid hormones, such as cortisol, testosterone, progesterone, estron, estradiol and estriol and the heart glycosides, such as digitoxin and digoxin. Furthermore, vitamins may be determined, especially Vitamin B12 and folic acid, as well as pharmaceuticals having strong protein bonds, such as, for example, anticoagulants, analgesics and salycilates.

The antibodies may be immobilized by means of different matrices. Examples of said matrices are agar, cellulose, glass particles, polyamides, polyacrylamides and copolymers of acrylamide. The latter is given particular preference. The advantages of antibodies enclosed in a matrix include the exclusion of interfering molecules of high molecular weights, the elimination of pipetting and centrifuging steps and the extended stability of immobilized antibodies at room temperature.

The micro-environment of the polymer matrix may be affected by the copolymerization of acrylamide with compounds capable of copolymerization with said acrylamide. The effect is the result essentially of hydrophobic and hydrophylic and electrostatic factors. By varying the polymer matrix through copolymerization, it is possible to substantially increase the bonding specificity of the antibody and to suppress undesirable cross reactivities. Copolymers of acrylamide and of one or several of the compounds acrylic acid, methacrylic acid, methacrylamide, their derivates and salts of acrylic acid and methacrylic acid, are especially preferred. The proportion of acrylamide in the copolymer may amount to between 1 and 99 mole %, preferably 5 to 95% mole %, and specifically 20 to 80 mole %. Copolymers of acrylamide and methacrylic acid and specifically those with a proportion of methacrylic acid of 20 to 60 mole %, are especially suitable. By using copolymers containing acrylic acid and methacrylic acid or their salts, a neutralizing or a buffer action for acid or alkaline solutions may be achieved additionally. Preferred salts are the alkali and/or alkaline earth salts.

Polymer matrices with immobilized antibodies may be prepared for example by adding a solution of the antibody to the monomer mixture. The initial mixture is, for example, polymerized by free radical polymerization and the polymer obtained comminuted, washed and dried.

In order to obtain a suitable pore size of the polymer matrix, the monomer concentration is varied. A monomer concentration in a range of approximately 20% leads to a pore size of approximately 7 to 10 Å.

BRIEF DESCRIPTION OF THE DRAWING

One embodiment of the invention particularly demonstrating an arrangement for the automated execution of the method of the invention is shown in the FIGURE.

DETAILED DESCRIPTION OF THE DRAWING

The immobilized antibody is contained in the small columns 5. These are mounted in an adapter plate 4. The charging and receiver vessels are arranged under the adapter plate and may constitute a combined unit 6. The columns 5 are connected by a pressure control means such as supply lines 7 and with vacuum/pressure pumps 1 and 2. The arrangement is controlled by an electronic control device 3. The plurality of columns 5 indicate a preferred arrangement of a multichannel system permitting the simultaneous determination of numerous samples.

The sample to be determined is placed in a reaction vessel and positioned under a prepared column containing the antibody. The following program is then set into operation by means of the control device:

One or both of the pumps run for a period of time creating negative pressure in supply lines 7 and column 5. In the process, the sample is thereby suctioned into the dry antibody gel.

Subsequently, there is a short pause interval. During this time, the swelling process of the gel takes place, together with the separation of free and protein-bound hormones. This interval or swelling phase is of the order of one minute.

During the next stage, both pumps are operating, with pump 1 transporting the elution liquid, for example, a buffer solution or water, and pump 2 transporting eluting liquid with the marked hormone (tracer). In the alternative, pump 2 alone may be in operation in the forward mode, i.e., creating positive pressure in the corresponding supply lines. In this manner, the protein fraction is eluted and the tracer is added simultaneously.

In order to prevent the mixing or dilution of the tracer prior to its addition to the gel with the buffer solution, the buffer solution and tracer solution are introduced through separate channels, said channels terminating directly above the gel. The elution and the addition of the tracer are to be performed as rapidly as possible in order to prevent the hormone from diffusing out of the gel. The amount of marked hormone added may be exactly calculated to produce the requisite accuracy of the determination. In an alternative method of measuring, the tracer need not be measured accurately if the steps are carried out within the saturation parameters of the antibody.

After the above described elution stage, there follows another pause interval, during which the marked hormone reacts with the remaining free bonding locations of the immobilized antibody.

This interval is usually of the order of approximately 10 minutes. Subsequently, elution with a pure buffer solution takes place with pump 1 operating in the forward mode. Through this elution, the hormone bound to the antibody and the unbound marked hormone are separated.

The radioactivity remaining in the elute or the columns is a measure of the concentration of the substances to be determined.

A calibration curve is established by subjecting known concentrations of hormones without protein to the same steps. A comparison of known determinations by means of dialysis and carbon adsorption shows that only free, diffusible hormones were measured in fact by the method of the invention.

One particular advantage discovered in the practical application of the method of the present invention is the elimination of strict temperature control to 0° C. to reduce dissociation. Measurements performed at 22° C. yielded identical values to those performed strictly at 0° C.

EXAMPLE 1

The invention is described in the following in more detail with the aid of an example demonstrating the determination of diffusible cortisol in serum.

A polymer gel with the immobilized antibody was prepared as described hereinafter. For each initial polymerizing mixture, the concentration was adjusted so that the total monomer concentration amounted to 3.13 mole/l. For an initial mixture, for example, 5 g acrylamide, 1.25 g N,N'-methylenebisacrylamide were dissolved in a beaker in 24 ml phosphate buffer (pH 7.2). In the preparation of copolymers, acrylamide was replaced in equal molar ratios by acrylic derivates. Following the addition of the antiserum in 1 ml phosphate buffer, the reaction was started with 0.15 mg riboflavin and 0.10 ml N,N,N'-tetramethylethylenediamine and UV radiation. During the irradiation period of approximately 45 minutes, the temperature was maintained under 50° C. The resulting gel block was then comminuted, washed with distilled water and dried.

In the determination of diffusible cortisol, two piston pumps with pumping rates of 0.68 ml/min. (Pump 1) and 0.5 ml/min. (Pump 2) were used, both being capable of forward and reverse motion. 60 mg of the dry anticortisolantibody gel were added in doses to small columns with inserted filters. From a reaction vessel, 320 $\mu$l incubation solution were suctioned with the pumps into the columns; said incubation solution containing the following substances dissolved in the phosphate buffer solution (pH 7.2): for the dose activity curve, unmarked cortisol in rising concentrations (0.56 to 17.66 p Mole), for the serum determination, dilute serum (1:12). The reaction temperature was maintained constant at 0° C. ±0.5° C. Protein elution with the aid of the pumps from the columns after a 4 minute swelling time with a 630 $\mu$l $^3$H-cortisol solution in scintillation dishes. Following a 10 minute incubation period with $^3$H-cortisol, the free cortisol was separated from cortisol bound to the antibody through elution with the pump 2 which carried the phosphate buffer solution (pH 7.2). The eluate (1 ml with an elution period of 3 minutes) was collected in scintillation dishes, diluted with 15 ml scintillation liquid and the radioactivity measured in a liquid scintillator. From the number of impulses per minute (cpm), the concentration of the free $^3$H-cortisol haptene was calculated. Thereafter, the content in diffusible cortisol of the serum was read from the dose activity curve.

EXAMPLES 2-5

Antibody matrices containing the following acrylic derivates were examined: 100% acrylamide, 60% acrylamide and 40% methacrylic acid ester, and 60% acrylamide and 40% methacrylic acid. The monomeric concentration in each case was 3.13 mole/l so that a pore size of approximately 0.8 to 1.0 nm was obtained. The particle size of the gel on the average amounted to approximately 400 $\mu$m. At a pumping rate of 0.5 ml/min, after 4 minutes 92% of the free haptene has been eluted.

The determination of diffusible cortisol in $\mu$g/100 ml yielded the following values under the different conditions:

| | |
|---|---|
| Normal | 1.5–2.5 |
| ACTH stimulation test | 4.5–10.8 |
| Dexamethasone Suppression | 0.15–1.0 |
| Pregnancies | 3.0–7.8 |

These values are in agreement with values determined by conventional methods, such as equilibrium dialysis.

EXAMPLE 6

The method of the invention was also used for the determination of testosterone. The working procedure followed in general was that of the determination of cortisol described above. However, 160 mg antibody gel was used, 1 ml incubation solution was suctioned into the columns and the protein solution was introduced with 1580 $\mu$l $^3$H-testosterone solution with a concentration of 270 pg/100 $\mu$l. A formal sensitivity of 10 pg/ml resulted.

What is claimed is:

1. A method for the determination of unbound hormones and pharmaceuticals comprising placing a solution containing unbound hormones, hormones bound to bonding proteins and bonding proteins into contact with a dry gel containing immobilized antibody; swelling the gel and reacting the unbound hormone with the antibody; eluting the hormones bound to bonding proteins and the bonding hormones; adding a solution containing a marked hormone; reacting the marked hormone with the antibody, and determining the marked hormone by radioimmunological evaluation.

2. The method of claim 1, wherein the antibody is enclosed in a polymer gel.

3. The method of claim 1 or 2, wherein the antibody is enclosed in an acrylamide polymer or acrylamide copolymer.

4. The method of claim 1, wherein the swelling takes place for a period of at least about one minute.

5. The method of claim 2, wherein the eluting solution and marked hormone are maintained separate from each other until addition to the polymer gel.

6. The method of claim 5, wherein the reacting of the marked hormone takes place for a period of about 10 minutes.

7. The method of claim 2, wherein the determining by radioimmunological evaluation comprises accurately measuring the amount of marked hormone employed, measuring the amount of marked hormone in the elute; separately measuring the amount of marked hormone in the polymer gel and comparing the measured values with a calibration curve obtained simultaneously by subjecting known concentrations of hormones without protein to the same steps.

8. The method of claim 1, wherein the temperature is maintained between about −5° C. and 5° C.

9. The method of claim 1, wherein the unbound hormones and pharmaceuticals determined are selected from the group consisting of thyroid hormones, steroid hormones, glycosides, vitamins, anticoagulants, analgesics and salycilates.

10. The method of claim 1, wherein the antibody is immobilized in a matrix selected from the group consisting of agar, cellulose, glass particles, polyamides, polyacrylamides and copolymers of acrylamide and copolymerizable monomers.

11. The method of claim 10 wherein the matrix has a pore size of from about 7 Å to about 10 Å.

12. The method of claim 1, wherein the marked hormone is a radiolabled hormone.

* * * * *